United States Patent [19]

Caputo et al.

[11] Patent Number: 5,830,134
[45] Date of Patent: Nov. 3, 1998

[54] METHOD AND EQUIPMENT FOR DETECTING PHYSICO-CHEMICAL PARAMETERS

[75] Inventors: Giuseppe Caputo, Castelluccio Inferiore; Giampiero Porro, Como; Stefano Rinaldi, Parma, all of Italy

[73] Assignee: Sorin Biomedica Cardio S.p. A., Saluggia, Italy

[21] Appl. No.: 725,912

[22] Filed: Oct. 4, 1996

[30]  Foreign Application Priority Data

Oct. 5, 1995 [IT] Italy .................................. TO95A0796

[51] Int. Cl.$^6$ .............................. A61B 5/00; G01N 21/31
[52] U.S. Cl. .......................... 600/322; 422/82.09; 436/68
[58] Field of Search ..................................... 128/633, 634, 128/664, 665; 422/82.05, 82.06, 82.07, 82.08, 82.09, 82.11; 436/68; 250/458.1; 600/310, 322, 323, 326, 473, 476

[56]  References Cited

U.S. PATENT DOCUMENTS

| | | |
|---|---|---|
| 4,200,110 | 4/1980 | Peterson et al. . |
| 4,430,565 | 2/1984 | Brogardh et al. . |
| 4,833,091 | 5/1989 | Leader et al. ............................ 128/634 |
| 5,001,054 | 3/1991 | Wagner ................................... 128/665 |
| 5,029,245 | 7/1991 | Keränen et al. . |
| 5,037,615 | 8/1991 | Kane . |
| 5,039,492 | 8/1991 | Saaski et al. . |
| 5,298,428 | 3/1994 | O'Rourke et al. .................... 422/82.11 |
| 5,379,764 | 1/1995 | Barnes et al. ........................... 128/633 |
| 5,453,248 | 9/1995 | Olstein ................................ 422/82.11 |

FOREIGN PATENT DOCUMENTS

| | | |
|---|---|---|
| 0586025 | 6/1993 | European Pat. Off. . |
| 2 255 639 | 11/1992 | United Kingdom . |
| WO 93/21592 | 10/1993 | WIPO . |

OTHER PUBLICATIONS

Upadhyaya et al., "Development and Application of Neural Network Algorithms for Process Diagnostics," *Proceedings of the 29th IEEE Conference on Decision and Control*, 6:3277–3282 (1990).

Taib et al., "Novel Technique to Improve Optical Fibre Sensor's Response for Industrial Applications," *IEE Colloquium on Advances in Sensors*, Digest No. 1995/232, pp. 13/1–13/6 (1995).

Herrala, Esko, et al., Imaging Spectrometer for Process Industry Applications, SPIE, vol. 2248, pp. 33–40 (1994).

Keller, Paul E., et al., Neural Network Based Sensor Systems for Manufacturing Applications, Advanced Information Systems and Technology Conferences in Williamsburg, VA, pp. 1–7, Mar. 29–30 (1994).

Keller, Paul E., et al., Three Neural Network Based Sensor Systems for Environmental Monitoring, IEEE Electro94 Conference in Boston, MA, pp. 1–8, May 10–12 (1994).

Keränen, Heimo, et al., Semiconductor Emitter Based 32–Channel Spectrophotometer Module for Real–time Process Measurements, SPIE, vol. 1266, pp. 90–98 (1990).

*Primary Examiner*—Jennifer Bahr
*Assistant Examiner*—Eric F. Winakur
*Attorney, Agent, or Firm*—Popovich & Wiles, P.A..

[57]  ABSTRACT

Physico-chemical parameters, such as pH, $pO_2$, $pCO_2$, % $O_2$, sat, etc., are determined with the use of a sensitive medium, such as a chromophore, having at least one optical property the profile of the spectrum whereof over a predetermined wavelength spectrum of optical radiation varies as a function of the parameter to be determined. The profile of the spectrum is analysed, for example by means of polychromatic sensor means acting on the medium's spectrum, which is preferably substantially continuous, so as to enable the analysis to be carried out with the aid of a profile-recognition function by typical pattern-recognition operations. The determination is thus rendered largely independent of numerous perturbing factors such as those resulting from the use of partially disposable monitoring units, thus eliminating the need for calibration steps.

81 Claims, 5 Drawing Sheets

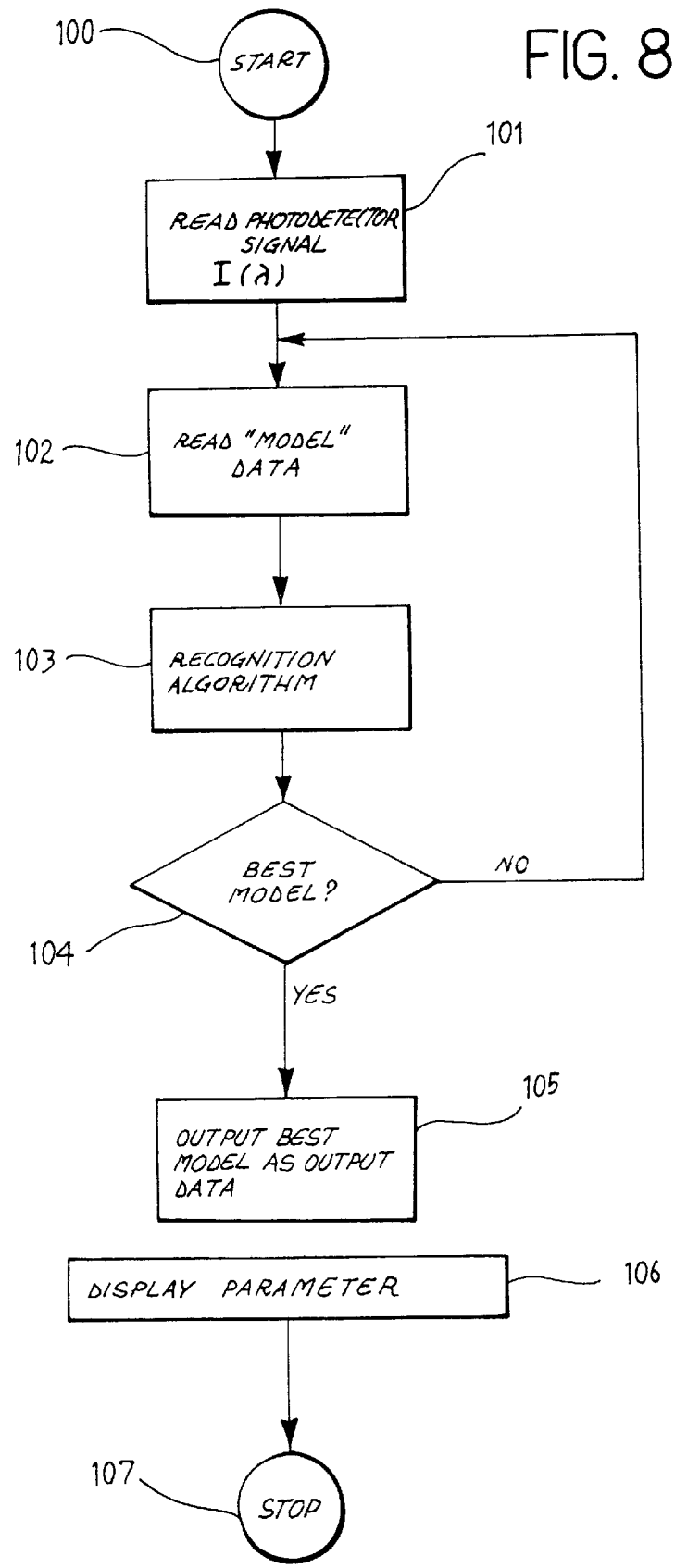

METHOD AND EQUIPMENT FOR DETECTING PHYSICO-CHEMICAL PARAMETERS

FIELD OF THE INVENTION

The present invention relates in general to the detection of physico-chemical parameters such as $pO_2$, $pCO_2$, pH, $\%O_2$ sat, $[K^+]$, $[Na^+]$, $[Ca^{++}]$, etc. with the use of a sensitive medium having at least one optical property (for example optical properties of reflectance, absorption or luminescence) which can vary as a function of the parameter to be detected.

DESCRIPTION OF THE PRIOR ART

In recent years various systems have been made available for the online determination (so-called monitoring), often in real time, of parameters such as those mentioned above (especially $pO_2$, $pCO_2$, and pH). Systems of this type, which may be usable in the intravascular environment and in operating theatres, are of considerable importance for biomedical applications such as the detection and monitoring of physico-chemical parameters of body fluids such as blood.

Usually the measuring technique of these systems is based on an evaluation of the optical absorption or emission of light at a specific, defined wavelength, the resolution and accuracy of the technique being limited by calibration procedures which may be very complicated, with the further risk that the measurement will be very sensitive to a wide number of interfering substances present in the biological specimen under examination and will be influenced by phenomena such as elution of the optically active substance or instrumental drift, etc. Usually such systems make use of a light source such as a xenon lamp, a bundle of optical fibres which convey the light to a measuring cell containing the sensitive medium, and other optical fibres which return the light to a photodetector, such as a PIN photodiode, which generates an electrical signal utilised for the determination.

For example, one commercially available system for the measurement of physico-chemical parameters of a blood flow, known by the trade name GasStat 100 (produced by the Bentley company) or by the trade name CDI System 400 (produced by the CDI- 3M Health Care company) includes a pH-sensitive part in which the sensitive medium is a cellulosic material to which hydroxypyrenetrisulphate (HPTS) is covalent bonded. The system further includes a $CO_2$-sensitive medium comprising a fine emulsion of a bicarbonate buffer (+HPTS) in a two-component silicone. A third medium, sensitive to oxygen, is also provided and is constituted by a solution of chemically-modified decacyclene (which is strongly damped by the oxygen) in a single-component silicone. The fluorescence of the three sensitive media can be correlated with the $pO_2$, pH and $pCO_2$ values by algorithms such as the Stern-Volmer or the Henderson-Hasselbach algorithms. Before use, it is necessary to calibrate the sensors by using a suitable calibration device containing two disposable gas cylinders with precisely determined $pO_2$ and $pCO_2$ values. During the calibration, the gases are bubbled through a bicarbonate buffer solution in the sensor chamber (cuvette) for about 7–10 minutes at ambient temperature in order to establish the calibration curve of the gases at two points. Current experience indicates that the device, which has a response time of the order of three minutes, is stable for about twelve hours of operation.

A system of the same nature is sold under the trade name Cardiomet 4000 by the English company Biomedical Sensors Ltd. This is a microprocessor-based system which is calibrated without the need to provide reference gases with precisely determined characteristics. Whilst precise calibration is not necessary for each patient, it is still necessary to perform a test cycle of several minutes periodically, at least once a day, and a complete calibration cycle, which requires about fifteen minutes, at least once a week.

U.S. Pat. No. 4,200,110 discloses a fibre-optic probe for pH-detection which can be implanted in tissue for the purpose of physiological studies. In general the equipment is based on the detection of absorption characteristics at a predetermined wavelength, such as 560, 485 or 600 nanometers. The possibility of utilising the absorption datum at 485 nm, which is almost invariable with pH, as a reference for normalising the reading at 560 nm is also explained (the generally similar behaviour of the graph of FIG. 1 in the region of these same wavelengths will be noted).

U.S. Pat. No. 5,039,492 describes a sensor for the optical determination of the pH and concentration of a gas which is also based on the monitoring of absorption at one or more predetermined wavelengths.

Finally, EP-A-0 586 025 provides a very wide and articulate review of various techniques for the measurement of parameters such as pH, $pCO_2$ and $pO_2$. In particular it reviews invasive colorimetric techniques, separation with semi-permeable membranes, electrode sensors/devices, transistors for the measurement of pH in vivo, various semi-invasive techniques, optical or spectroscopic determinations, pulsed oximetry, spectroscopic determinations of pH in non-biological systems with associated algorithms for spectral analysis. In particular, the process which constitutes the subject of EP-A-0 586 025 provides for the direct irradiation in vivo, in a non-invasive manner, of tissue containing blood so as to enable the differential attenuation of two or more wavelengths of optical radiation within the range 500 to 2400 mm, utilised to illuminate the tissue, to be monitored. Although the associated description makes repeated reference to the use of spectral analysis in general terms, from a reading of the examples it can be seen that tissue illumination is effected only at a restricted number of discrete wavelengths (typically two or three, with a maximum value of seven wavelengths) Since the detected property is, in any case, always attenuation, which can be influenced not only by the parameters which it is desired to determine but also by parameters of the apparatus (essentially the optical coupling between, on the one hand, the light source and/or the photoelectric sensors and, on the other, the tissue subjected to analysis, this in practice being the tip of a patient's finger inserted into a suitable detector support), it is always necessary to perform a preliminary calibration step. In fact, the determination is primarily a determination of tendency or trend factors of the detected parameters rather than the identification of absolute values.

From the above it is apparent that, if the determination of a given physico-chemical parameter is based on variations in optical attenuation or, what is practically equivalent, absorption and/or propagation, and thus solely on the intensity of a signal indicative of this attenuation, at one or more given wavelengths, the determination is open to numerous sources of inaccuracy. Indeed, the intensity of the signal in question may vary not only because of variations in the parameter or parameters to be determined, but also because of various external factors such as, for example:

variations in the optical coupling between a light source and the optical fibre or fibres which usually convey the radiation used for the monitoring from and to the sensitive medium, variations in the propagation of the radiation along these fibres, variations in the optical coupling between the output of these fibres and the sensitive medium and/or in a complementary manner, variations in the coupling between the sensitive medium and the optical fibres which convey the radiation from the sensitive medium to the monitoring unit, variations in the propagation of the radiation along these fibres and, again, variations in the coupling between these fibres and the photodetector, all of which constitute perturbing factors which it is necessary to take into account, the effect of any variations being annulled by means of a calibration process performed on a medium having known properties before the monitoring process proper is started. The problem is made particularly acute by the fact that, as already mentioned, systems such as those described above are intended to be made and used not only as laboratory apparatus capable of operating in precise predetermined conditions which are repeatable with good reliability, but in the form of equipment intended to be used in the operating theatre or, in any event, outside the laboratory. For these uses it is almost imperative to arrange for the part of the system containing the sensitive medium or media intended to be exposed to the fluids, such as blood etc, the parameters whereof are the subject of the monitoring, to be made in the form of a disposable unit which can be coupled to the system when needed in conditions which may vary according to how the unit is assembled at the time, this often being in urgent conditions.

The solution, as presented for example in U.S. Pat. No. 4,200,110 of utilising two different monitoring wavelengths and normalising the monitored datum at one wavelength with the aid of that at the other wavelength, resolves the problems indicated above only to a minimum extent: it is not mentioned at all, for example, that the normalised value obtained in the manner described above is invariant with respect to one or more perturbing phenomena so that it is still necessary to carry out a relatively long calibration process fairly often. This is essentially true also for solutions which use more sophisticated processing algorithms, such as that described in EP-A-0 586 025.

OBJECTS AND SUMMARY OF THE INVENTION

The present invention has the object of solving the above problems in a radical manner. According to the present invention this object is achieved by a method and equipment having the characteristics specifically set out in the following claims.

As an illustration of the principle on which the invention is based, reference may be made to the graph of FIG. 1 which shows, by way of example, typical photoabsorption spectra (absorption values on the ordinate) for a sensitive medium constituted by a mixture of bromothymol blue and brilliant yellow at different pH values with variations in the wavelength expressed in nanometers (given on the abscissa). As can be seen, one is dealing with the typical spectroscopic behaviour of a chromophore at different pH values. Spectra such as that shown in FIG. 1 can be obtained (by conventional laboratory spectrographic techniques) not only, for pH and other parameters expressly mentioned above but also for numerous other physico-chemical parameters and/or for a wide variety of sensitive media, and also for optical characteristics other than absorption, such as luminescence or chromophoric characteristics.

It is therefore possible, by detecting and, optionally, measuring variations in one or more optical properties of the sensitive media, to carry out a corresponding process of detecting and measuring one or more parameters which it is wished to determine.

The above is an explanation of a widespread body of scientific and technical knowledge which constitutes the foundation for the invention. As will become more apparent below, the invention relates specifically to the choice of the type of behaviour of the sensitive medium used for the monitoring as well as to the criteria and manner of detection of the optical properties used for the monitoring: this essentially leaves out of consideration both the nature of the parameter investigated and the specific choice of the sensitive medium adopted for the detection. One can even state, with substantial adherence to reality, that the invention is entirely open as regards these specific choices.

In this respect it should be stated that expressions such as "optical", "light" etc, as utilised in the present description and in the appended claims, are not in any way intended to be limited to the spectrum of visible radiation but also extend at least to the adjacent bands of electromagnetic radiation, such as the infra-red and ultraviolet. It is likewise evident that, hereinafter and also in the appended claims, where reference is made to a "wavelength spectrum" this term should also be understood to include the corresponding frequency spectra and/or associated wave number spectra (wavelength, frequency and wave number being quantities derivable from, and functionally linked to, one another).

It is important, for the purposes of the invention, that the variations in the optical property of the sensitive medium utilised for the monitoring, induced by variations in the parameter to be determined, do not lead simply to an overall variation in the intensity of the monitored signal, that is to a simple upward or downward translational movement of this signal at the monitoring frequency or frequencies. On the contrary, in the solution of the invention, an optical property of the sensitive medium is used whereby a variation in the parameter to be determined corresponds to a variation in the profile of the optical property (and thus not just an upward or downward translational movement but also a deformation, reshaping on one or more at least partial local rotations etc) over the wavelength spectrum (or frequency spectrum which is equivalent) of the optical radiation utilised for the monitoring.

The solution of the invention thus envisages the monitoring of variations in the profile of the property or properties (the significance attributed to the term "optical" has already been mentioned in the introductory part of the specification) and therefore the monitoring is preferably carried out not just at individual wavelengths (or frequencies or wave numbers which, as has been mentioned, are equivalent) but over a broader optical spectrum defined as a "polychromatic spectrum, which is substantially free from discontinuities". By this term it is intended here to define a spectrum and associated detector means and, if present, light means which operate over an extensive plurality of wavelengths (or frequencies or wave numbers) and not just at one or two wavelengths of approximately monochromatic radiation as is the case in prior-art solutions, and with spectral characteristics of sensitivity and/or overall emission which are substantially free from gaps or troughs such as those which would be caused by the simple combination of a few substantially monochromatic sources or sensors.

A source of optical radiation having characteristics of this nature is described, for example, in the paper "Semiconductor emitter based 32-channel spectrophotometer module for real-time process measurements" by H. Keränen and J. Malinen presented at Eco—The Hague, The Netherlands, 14–15 Mar. 1990 and published in SPIE Volume 1266, In-Process Optical Measurements and Industrial Methods (1990) pages 91 to 98 as well as in PCT/FI88/00103).

A photodetector having characteristics of the same nature is described in the paper "Imaging spectrometer for process industry applications" by E. Herrala, J. Okkonen; T. Hyvärinen, M. Aikio and J. Lammasniemi, published in SPIE volume 2248, pages 33–40.

The fact that a spectrum of the type specified above is used, allows the entire profile of the property, such as the absorption properties shown in FIG. 1, to be monitored, if necessary, over a wide range of wavelengths $\lambda$, such as the spectrum from about 270 nm to about 700 nm shown in FIG. 1, the result not being limited, as is usually the case in the prior art, to values detected at one or two wavelengths. In each case, a functionally equivalent result may be obtained by known means, even without sensor means and/or illuminating means which are able, by their characteristics, to cover the said polychromatic spectrum substantially without discontinuities. The data relating to the profile of the spectrum of the property used for the detection over such a polychromatic spectrum may in fact be reconstructed by an algorithm (in known manner) from the data detected at specific distinct values provided a sufficient number of samples is available. In each case, in the following detailed description of one possible embodiment of the invention, reference will be made for simplicity to solutions in which the sensors and/or the sources used provide physical cover for the said spectrum. The invention must not however be understood as limited to this specific embodiment, as indicated above.

Equipment which operates in accordance with the invention has a memory in which, for each parameter detected (monitored) and as a function of the sensitive medium used, there is stored a set of models of profiles of the spectrum of properties monitored over a wide spectrum of observation, each corresponding to a different value of the parameter in question.

The profile detected at any instant by the sensor means is compared (over a wide range of wavelengths) with the set of models stored in the memory of the equipment, or at least with some of these models, so as to identify (according to the criteria currently used for carrying out functions termed "pattern recognition", including solutions which make use of neural networks) that model, from among the various models, which can be considered as having the greatest similarity to the profile detected at that instant, or that profile which can be likened to it with the greatest probability. The model thus selected (possibly with the use of decisional techniques of the type based on "fuzzy" sets) is identified as the read datum and used to identify the value to be attributed to the parameter being detected. As regards the possible use of neural networks, reference may be usefully had, by way of example, to the paper "Three Neural Network Based Sensor Systems for Environmental Monitoring" by P. E. Keller, R. T. Kouzes and L. J. Kangas presented at the IEEE Electro 94 Conference, Boston, Mass. U.S.A.; 10–12 May 1994, or to the paper, by the same authors, "Neural Network Based Sensor Systems for Manufacturing Applications" presented at the Advanced Information Systems and Technology Conference of Williamsburg, Va. U.S.A.; 28–30 Mar. 1994.

In summary, with reference to the graph illustrated in FIG.1, if it is found that the profile detected at any instant corresponds, with maximum probability or likelihood, to that curve on the graph which has the highest value in the central part ($\lambda$=407 nm) of the graph of FIG. 1 and the lowest value at the right hand and ($\lambda$=500–700 nm) of the same graph, then the system identifies the pH used as the read datum with the pH value of this specific curve, used as the model, that is, 6.011.

The recognition action thus effected leaves completely out of consideration attenuation or like perturbations which may, for example, result in an upward or downward translational movement of the profile detected at that instant or to amplification or attenuation of the signal: what matters, for the recognition, is the shape, or profile, of the spectrum in its entirety, that is, the form of the curve and not just the absolute values of this profile resulting from upward or downward movement at one or even a few points, that is in the sense of amplification or attenuation of the relative signal.

The data base constituted by the said models used for the recognition of configurations relative to a parameter and to a respective sensitive medium is stored in the equipment during its setting up, without necessarily requiring further calibration during normal operation.

Once stored in the data base, the set of possible profile models of a specific optical property which varies as a function of the variations in a predetermined parameter to be detected with the use of a specific sensitive medium, which set of models is determined once and only once, is used in the equipment without requiring further modifications or changes.

Ad abundantiam, it will again be noted that, even though the present description describes the invention with reference to wavelength spectra, the invention itself may be described and claimed in an entirely identical manner with reference to frequency spectra, wave number spectra and possibly spectra of other comparable physical quantities as is completely evident to an expert in the art.

BRIEF DESCRIPTION OF THE DRAWINGS

The invention will now be described, purely by way of non-limitative example, with reference to the appended drawings, in which:

FIG. 8 is a schematic illustration in the form of a flow diagram showing the manner of operation of a processing unit which carries out a configuration recognition function in equipment of the invention.

DETAILED DESCRIPTION OF ONE EMBODIMENT OF THE INVENTION

Figure 2:
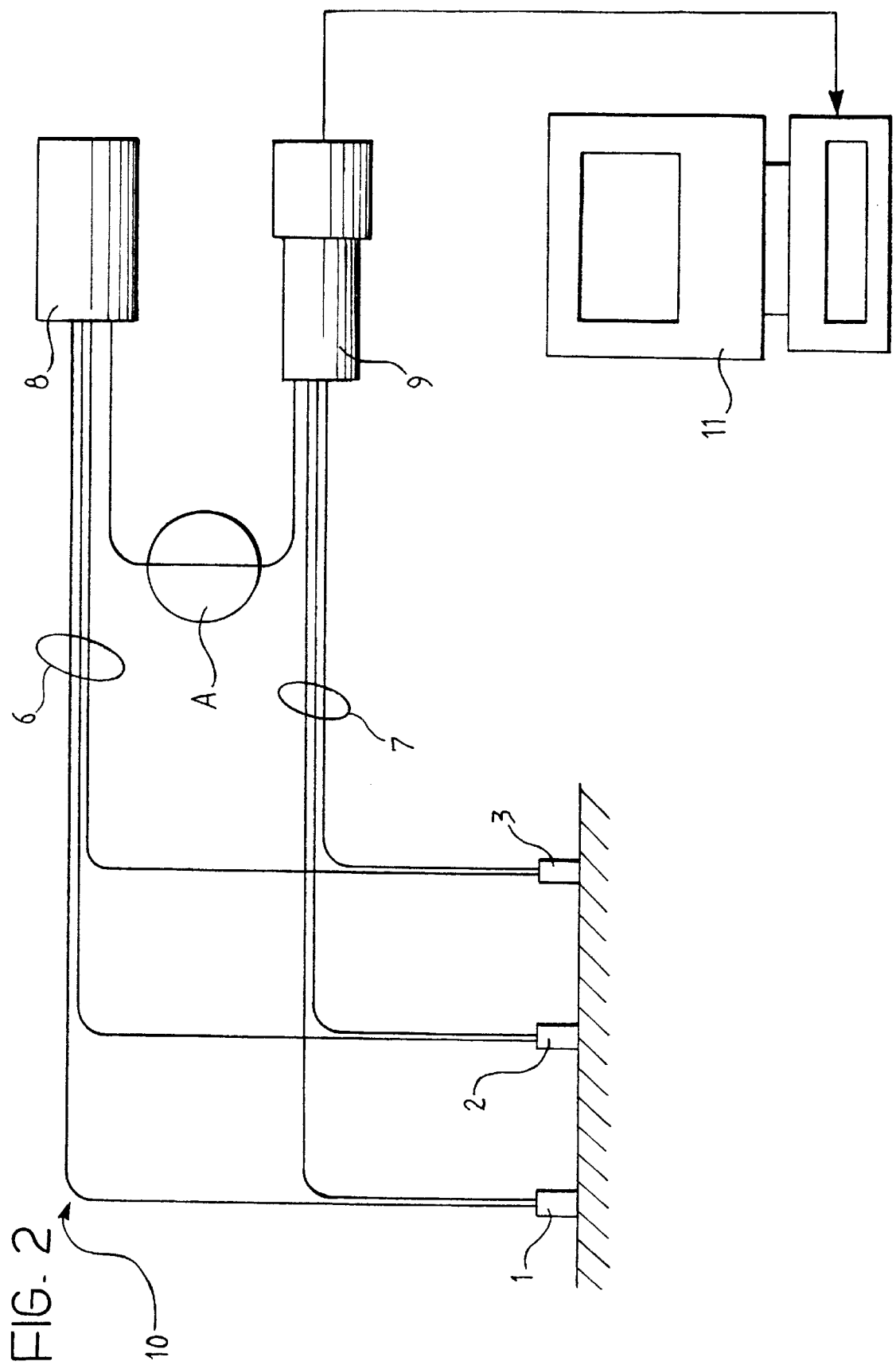
FIG. 2 is a schematic illustration of a possible configuration of equipment according to the invention.
Figure 3:
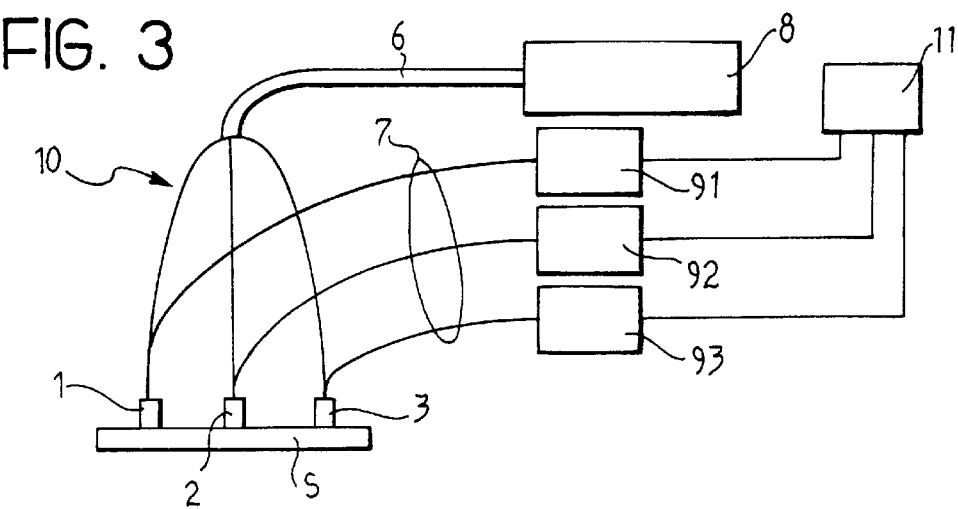
FIGS. 3 and 4 illustrate, again schematically, two possible simplified variants of equipment according to the invention.
Figure 4:
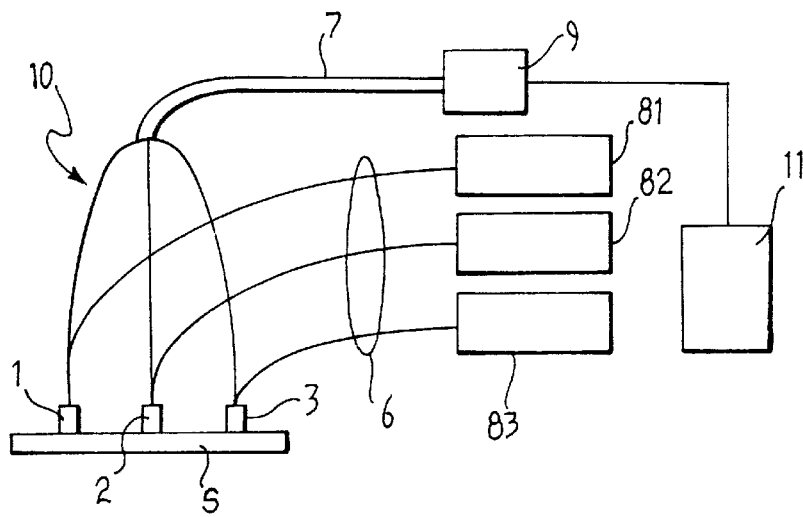

In FIGS. 2 to 4, reference S generally indicates the medium (for example blood or serum) of which it is wished to detect predetermined physio-chemical parameters such as the pH, $pCO_2$, $pO_2$ etc. This medium may be constituted either by a static sample (for example a quantity of blood taken from the body of a patient) or a flow of this medium in, for example, a duct in an extracorporeal circulatory system of a patient during an operation.

According to known criteria, the medium S subjected to the monitoring is exposed (for example by direct physical contact or with the interposition of a semi-permeable or gas-permeable membrane) to one or more monitoring units 1, 2, 3 (there may be any number of these units according to the specific applicational requirements), each of which is provided for the determination of a respective physico-chemical parameter, the determination being carried out optically with the use of a respective sensitive medium. For this purpose reference may usefully be made to the summary of known commercial apparatus given in the introduction to the present specification.

Figure 5:
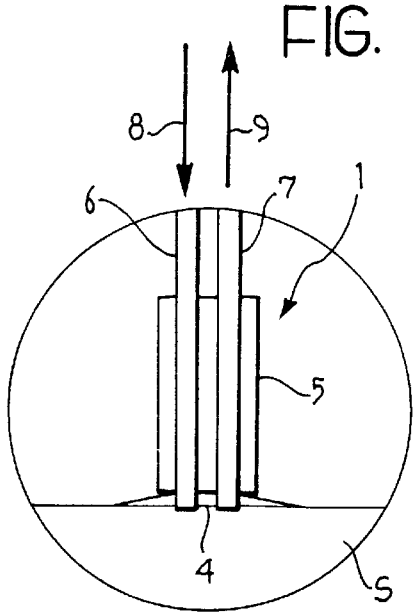
FIG. 5 is a detailed view illustrating possible details of the equipment of FIGS. 2 to 4.

FIG. 5 illustrates schematically the structure of one of the units in question, here identified as the unit 1. In essence (one is reminded that the representation given here is completely schematic and made with the primary intention of facilitating an understanding since the specific details are known to the expert in the art and are not themselves relevant for an understanding of the invention) the unit 1 includes a sensitive medium such as, for example, a chromophoric medium 4 having at least one optical property (for example absorption or chemiluminescent or chromophoric properties) having an optical wavelength spectrum, the profile of which varies selectively as a function of a respective physico-chemical parameter of the medium S being monitored.

Figure 1:
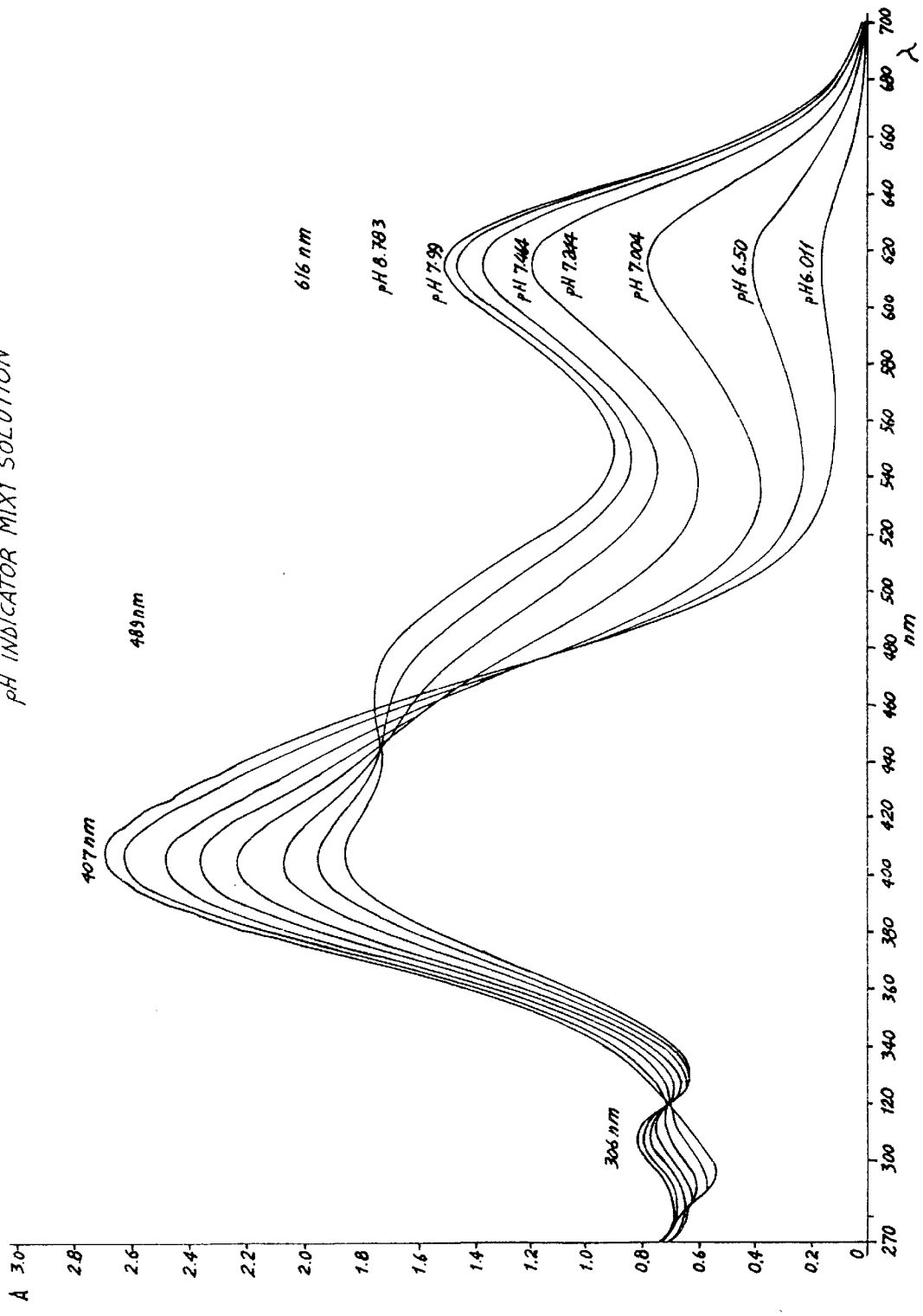
FIG. 1 is a graph which has already been discussed extensively above.

By way of example, the material 4 may be a pH indicator whose absorption and/or reflectance properties have a profile which varies as a function of wavelength in a manner similar to that shown in the graph of FIG. 1.

An optical coupling unit, generally indicated 5, is connected to the ends of respective optical fibres 6, 7 the function of which is essentially to convey optical radiation from a source 8 and radiation to be sent to a photodetector 9 (for example a spectrophotometer, a photodiode or the like) to and from the chromophoric material 4.

The optical coupling units 5, their fibres 6, 7 as well as the source 8 and the detector 9 preferably (and according to known criteria) constitute the fixed parts of the monitoring equipment generally indicated 10. The chromophoric material 4 and its support (such as a tube, dish or cuvette etc) and the part of the monitoring unit intended to receive the medium S to be monitored are preferably formed as a disposable element which can be replaced every time a fresh monitoring operation is to be carried out, for example because of a change in patient.

FIGS. 2 to 5 relate, by way of example, to an embodiment in which the equipment 10 includes both excitation, or stimulation, means (that is the light source a of FIGS. 2 and 3) for exciting the sensitive medium, such as the chromophoric material 4, and optical monitoring means (detector 9 of FIGS. 2 and 4). This arrangement appears generally preferable since, in most cases, the optical properties used for the monitoring are properties such as absorption or other chromophoric properties linked essentially to criteria whereby optical radiation directed at or through the sensitive medium is modified or altered by the sensitive medium itself.

At least in principle, to monitor some physico-chemical parameters, it is possible to make use of optical properties which do not require specific excitation (illumination) of the sensitive medium: this is true, for example, in the case of some chemiluminescent properties in which the emission of radiation by the sensitive medium is stimulated chemically and not by optical radiation directed at the sensitive medium itself or, in addition, in particular situations of use in which, for example, the excitation may be effected simply by ambient light and thus without the need to provide a specific light source for illuminating the sensitive medium 4.

In each case, in the description below, specific reference will be made to the most general case in which the equipment 10 also includes a light source such as the source 8 of FIG. 2 or the sources 81, 82 and 83 of which more will be said below.

In the embodiment illustrated in FIG. 2, which is that considered most complete at present, the source 8 is a source such as that described in the article by Keränen and Malinen cited above while the detector 9 is of the type described in the paper by Herrala, Okkonen, Hyvärinen, Aikio and Lammasniemi, also mentioned in the introduction to the present specification.

One is dealing, as much for the source 8 as for the detector 9, with devices which make use of solid-state optical sources/detectors and which are able to cover a wide spectral band substantially continuously, virtually (for the detector) the band between about 380 nm and about 1800 nm so as to achieve a multichromatic monitoring function over a substantially continuous spectrum in the terms clarified above.

In summary, the source 8 comprises a two-dimensional array of light emitting diodes (LED) the elements of which have respective emission spectra centred about different frequencies; optical radiation from the array is directed through an optical system including a spherical mirror associated with a main prism and with a regulating prism having an associated reflecting grating with a transparent window so that optical radiation is output over a substantially continuous spectrum between wavelengths of about 810 nm and 1060 nm. This spectrum corresponds to the superposition of the individual emission spectra of the diodes in the array, the frequencies of which are staggered in such a way as to cover the overall spectrum desired as continuously as possible.

This polychromatic radiation is directed to the units 1, 2, 3, and hence, through the fibres 6, to the respective sensitive media such as the chromophoric material 4. The radiation, modified by passage through and/or reflection by the various sensitive media (thus modified as a function of the parameters of the medium S which it is wished to monitor), is collected by the same units 5 and sent through the fibres 7 to the photodetector 9. As already stated, this detector may be a visualising spectrometer based on a prism/grating/prism element (PGP) which acts as a dispersive element and has a respective associated optic which enables a monitoring signal to be sent to a CCD type photodetector matrix, the monitoring signal being distributed on two axes indicative respectively of the spectral coordinates and the spatial coordinate of the monitoring signal.

The detector 9 may thus supply a processing unit, such as, for example, a microprocessor or a personal computer 11, with respective electrical signals (usually converted into digital form by an analog/digital converter—of known type—not explicitly shown in the drawings) indicative, for each monitoring unit 1, 2, 3, of the shape or profile of the spectrum of the optical characteristic monitored by each respective sensitive medium as a function of the respective parameter.

In other words, the processing unit 11, for each of the parameters being monitored, receives a signal which represents a curve or profile, such as one of the curves or profiles illustrated in relation to pH variations in the graph of FIG. 1. More precisely, the processing unit 11 receives from the detector 9 a curve or profile corresponding to the result of a detection at that instant. During processing, this same unit 11 in a manner typical of pattern recognition processes, derives a known value of the parameter from the curve or profile detected at that instant. This operation is carried out by a recognition process based on curves or profiles stored in the unit 11 itself as typical models.

The solution illustrated schematically in FIG. 2 preferably provides for the interposition, between the source 8 and the detector 9, of a direct connection, indicated A, which can be used for calibration purposes, essentially to regulate the sensitivity of the detector 9 in dependence on the intensity of the radiation emitted by the source 8.

It is however entirely obvious that this calibration function is an ordinary regulating function of the system 10 which can be likened, for example, to the regulation of the luminosity or contrast of a cathode ray tube or an automatic control system for the volume. This function, which has nothing to do with the complex calibration procedures of prior-art systems, in which the whole of the equipment 10 would have to be calibrated from time to time with the use of one or more test media S to take account of possible variations or perturbations which arise from time to time, for example because the disposable part of the system is changed. As already stated, the solution of the invention enables all these calibrating steps to be eliminated.

The solution illustrated in FIG. 2, while being preferred in overall terms of efficiency and compactness of the equipment 10, may be burdensome to manufacture particularly because of the need to use two-dimensional arrays of solid-state detectors and sources for the detector 9 and the source 8 respectively, with respective associated optics for concentrating/dispersing the radiation.

The schematic diagrams of FIGS. 3 and 4 show alternative solutions in which both the detector 9 (FIG. 3) and the source 8 (FIG. 4) are subdivided into several detectors (91, 92, 93) or several sources (81, 82, 83) respectively, each of these detectors and/or each of these sources being dedicated to receiving/transmitting radiation directed from or towards one of the monitoring units 1, 2, 3.

Naturally the teachings of FIGS. 3 and 4 may be combined to give rise to a system in which there is a plurality of sources and a plurality of receivers.

Whatever the specific solution adopted, the variants in question enable the structure of the array of sources or the array of detectors to be simplified, for example by making use of arrays of LEDs or photodetectors (for example in the form of CCD arrays) with one-dimensional, linear characteristics.

The use of one-dimensional arrays has the advantage of lower costs, a better single/noise ratio and a less complex electronic control system for the equipment.

Figure 6:
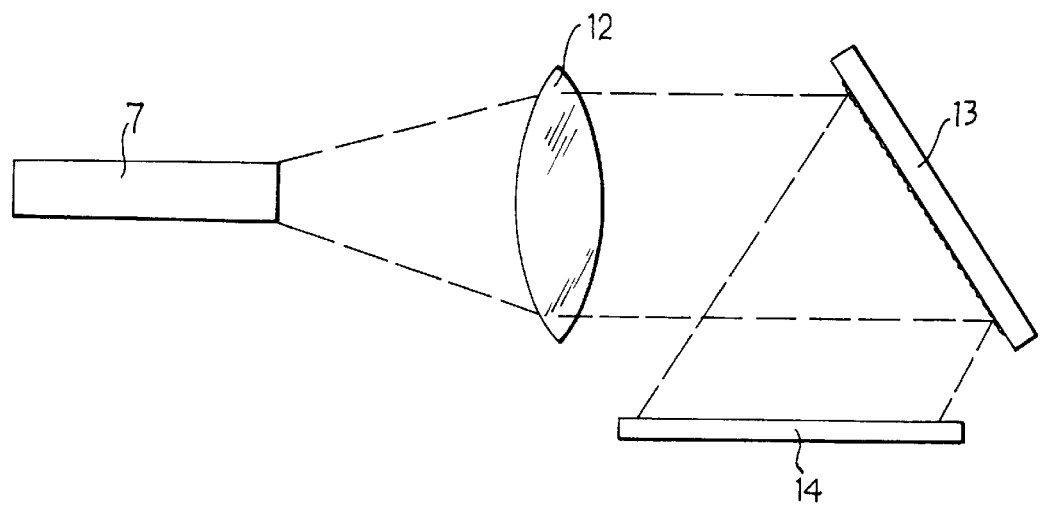
FIG. 6 is a schematic illustration of a possible embodiment of one of the elements illustrated in FIG. 4.

In practice, as illustrated in FIG. 6 with reference to one of the photodetectors 91, 92, 93 (in this specific case reference is made to the photodetector 91), the structure is simplified by the simple provision of a focusing optic 12 at the output of the respective fibre 7, which sends radiation to a grating 13 which in turn directs the radiation on to a linear array of photodetectors, for example, a linear CCD array indicated 14.

Figure 7:
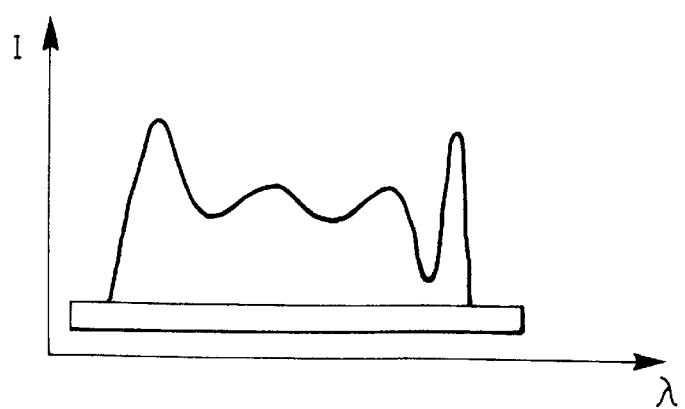
FIG. 7 illustrates the profile of a spectrum of a signal obtainable with the equipment illustrated in FIG. 6.

With this arrangement it is possible for each of the detectors 91, 92, 93 to send a monitoring signal to the processing unit 11, the signal representing a spectrum such as that illustrated in FIG. 7 in which the wavelength ($\lambda$) is shown on the abscissa and an optical parameter, such as the reflectance or absorption of the sensitive medium, is shown on the ordinate and is represented by the intensity I of the optical radiation which is incident on the various portions of the linear sensor 14.

The processing unit 11 performs the recognition function schematically shown in the flow diagram of FIG. 8 on this signal.

In this respect it should also be remembered that, during the initial setting up of the system 10, sets of curve profiles of the type shown in FIG. 1 are stored in the memory of the processing unit 11 (for example by loading from an external support such as a diskette), these profiles corresponding to changes in a particular optical property (for example absorption) as a function of the wavelength $\lambda$ for various values of the parameter (pH in the case of FIG. 1) which it is wished to determine.

During the carrying out of each measurement or determination cycle, starting with a start step indicated 100, the unit 11, in a first step 101, reads the monitoring signal I ($\lambda$) supplied to it by one of the detectors, for example the signal shown schematically in FIG. 7 with reference to the detector 91; a signal of this type, in a two-dimensional array, can be obtained for each parameter even from a more complex source such as that indicated 9 in FIG. 2.

The step indicated 101 is followed by a series of steps, indicated 102, 103 and 104, which correspond to a typical "pattern recognition" function, aimed essentially at identifying the curve or profile read in the step 101 with one of the profile or spectra models stored in the unit 11.

By way of example (as is well known to experts in the art of "pattern recognition", the possible variants are practically infinite—see also the bibliographical references on possible use of neural nets cited in the introductory portion of the description), a process is explained here, by way of example, which provides for an ordered reading of the models from the memory, carried out in the step 102, which is followed by a comparison, carried out in the step 103, of the profile read in the step 101 with the profile read at that instant in the step 102. This comparison may be carried out in accordance with various criteria, for example with the use of tests of the type currently called "template tests", or with approximation algorithms of the type currently termed "best fit" or "best match" types or, yet again, with maximum likelihood algorithms of the probabilistic type. For example, as a result of the comparison, there are determined the deviations of the profile detected (step 101) from the profile of the optical property's spectrum over the wavelength spectrum used for the monitoring.

As is well known one is dealing with algorithms which may be made completely independent of any amplification or attenuation of the signal, as well as of displacements or translations of the curves which are compared, for example as a result of a displacement along the ordinate, in the graph of FIG. 1, due to anomalous changes in the level of the signal conveyed by the fibres 6 as a result, for example, of imperfect optical coupling.

The step 103 is concluded by a selection step 104 in which, essentially, it is decided whether the model used at that instant for the comparison may be considered the optimum for the purposes of identification with the profile read in the step 101. The comparison carried out in step 104 is in fact repeated cyclically so as to allow at least virtually all the models memorised to be taken into account until the model considered best is identified.

At this point, in a subsequent step indicated 105, the model selected as the best is identified as that corresponding to the profile read in the step 101. The respective value of the parameter determined is selected as the read parameter intended to be presented to the outside, for example by visual display (step 106) on the visual display unit associated with the processing unit 11. At this point, the system switches into a waiting phase 107 ready for the reading of a new curve or profile and the repetition of the process described above. Clearly the operations described above may be carried out almost simultaneously or concurrently on various monitored signals so as to enable several read parameters to be displayed simultaneously, in a similar manner.

With regard to the selection, the value attributed to the physico-chemical parameter is determined by interpolation as the value corresponding to the minimum deviations determined of the profiles in the data base from the profile detected at that instant.

Naturally, the principle of the invention remaining the same, the constructional details and forms of embodiment may be varied widely with respect to those described and illustrated, without thereby departing from the scope of the present invention. This is true particularly with regard to the selection of the particular pattern recognition algorithms used, and especially with regard to the possible use of recognition systems which are not strictly algorithms, such as, for example, systems based on the use of neural networks.

What is claimed is:

1. A method for determining the value of at least one physico-chemical parameter of a medium comprising:

(a) providing a medium having at least one physico-chemical parameter;

(b) providing a sensitive medium having at least one optical property in which a variation in at least one physico-chemical parameter of the medium produces a variation in a profile of a spectrum of the at least one optical property of the sensitive medium over at least one predetermined wavelength spectrum range of optical radiation;

(c) exposing the medium to the sensitive medium;

(d) monitoring the at least one optical property of the sensitive medium to obtain a monitored profile of the spectrum over the at least one predetermined wavelength spectrum range of optical radiation;

(e) comparing the monitored profile of the spectrum of the at least one optical property with a plurality of predetermined profiles which correspond to a plurality of values of the at least one physico-chemical parameter of the medium; and (f) determining the value of the at least one physico-chemical parameter by comparing the monitored profile of the spectrum of the at least one optical property with the plurality of predetermined profiles, wherein the comparison of the monitored profile with the plurality of predetermined profiles is independent of any translational movement, amplification, attenuation, or displacement of the monitored profile of the spectrum of the at least one optical property of the sensitive medium.

2. The method according to claim 1, wherein the wavelength spectrum range is a wavelength spectrum range of polychromatic optical radiation substantially without discontinuities.

3. The method according to claim 2, wherein said polychromatic spectrum substantially free from discontinuities extends over the wavelength range of between about 380 and about 1800 nanometers.

4. The method according to claim 2, wherein said polychromatic spectrum substantially free from discontinuities extends over the wavelength range of between about 270 and about 700 nm.

5. The method according to claim 2, wherein said polychromatic spectrum substantially free from discontinuities extends over the wavelength range of between about 810 and about 1060 nm.

6. The method according to claim 1, wherein the monitoring step (d) is performed using a solid-state optical sensor.

7. The method according to claim 6, comprising providing the solid-state sensor in the form of an array of photosensitive elements.

8. The method according to claim 1, comprising illuminating the sensitive medium with optical radiation at least over the wavelength spectrum range and detecting the at least one optical property by monitoring the changes induced by the sensitive medium in the spectrum of the reflected, transmitted or emitted radiation relative to the spectrum of the illuminating radiation.

9. The method according to claim 8, comprising generating the optical radiation over the wavelength spectrum range using a solid-state light source.

10. The method according to claim 9, comprising providing the solid-state light source in the form of an array of solid-state luminescent elements.

11. The method according to claim 1, wherein the at least one optical property is selected from the group consisting of chemiluminescent and chromophoric characteristics of the sensitive medium.

12. The method according to claim 1, wherein the determination of the value of the at least one physico-chemical parameter from the monitored profile of the optical property of the sensitive medium over the wavelength spectrum range is effected by a pattern recognition procedure selected from an algorithmic type or a non-algorithmic type.

13. The method according to claim 1, further comprising:

(a) creating a data base containing a plurality of profiles of the spectrum of the at least one optical property over the wavelength spectrum range for different values of the at least one physico-chemical parameter;

(b) entering the data base in a memory of a processing unit;

(c) identifying using a recognition procedure a best fit profile to the monitored profile from the plurality of profiles in the data base entered in the memory; and (d) indicating the value of the at least one physico-chemical parameter which corresponds to the best fit profile.

14. The method according to claim 13, wherein the identifying step is carried out by determining the departures of the optical property's spectra over the wavelength spectrum range from the monitored profile.

15. The method according to claim 14, wherein the value of the at least one respective physico-chemical parameter is determined by interpolation as that corresponding to the minimum departures of the profiles of the plurality of profiles in the data base from the monitored profile.

16. The method according to claim 1, wherein the physico-chemical parameter is selected from the group consisting of $pO_2$, $pCO_2$, pH, percent $O_2$ saturation, concentration of $K^+$, concentration of $Na^+$, and concentration of $Ca^{++}$.

17. The method according to claim 1, wherein the medium is blood.

18. The method according to claim 17, wherein the blood is in an extracorporeal circulatory system.

19. The method according to claim 1, wherein the medium is serum.

20. The method according to claim 1, wherein the monitoring of the at least one optical property of the sensitive medium and the comparing of the monitored profile with the plurality of predetermined profiles are both conducted in real time.

21. Equipment for monitoring the value of at least one physico-chemical parameter of a medium using a sensitive medium having at least one optical property that varies in dependence on the at least one physico-chemical parameter of the medium, the equipment comprising:
(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;
(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and
(c) a processor for deriving from the monitored signal and a plurality of predetermined profiles which correspond to a plurality of values of the at least one physico-chemical parameter a monitored datum indicative of the at least one respective physico-chemical parameter of the medium,
wherein the monitored datum is derived from the monitored signal independent of any translational movement, amplification, attenuation, or displacement of the monitored profile of the spectrum of the at least one optical property of the sensitive medium.

22. The equipment according to claim 21, wherein the wavelength spectrum range is a wavelength spectrum range of polychromatic optical radiation substantially without discontinuities.

23. The equipment according to claim 22, wherein said polychromatic spectrum substantially free from discontinuities extends over the wavelength range of between about 270 and about 700 nm.

24. The equipment according to claim 22, wherein said polychromatic spectrum substantially free from discontinuities extends over the wavelength range of between about 810 and about 1060 nm.

25. The equipment according to claim 21, wherein the optical monitor comprises a solid-state sensor.

26. The equipment according to claim 25, wherein the solid-state sensor comprises an array of solid-state photosensitive elements.

27. The equipment according to claim 26, wherein the array of photosensitive elements is a two-dimensional array.

28. The equipment according to claim 26, wherein the array of photosensitive elements is a one dimensional array.

29. The equipment according to claim 28, wherein the one-dimensional array comprises a beam concentrator for concentrating a light beam on the array of photosensitive elements.

30. The equipment according to claim 29, wherein the beam concentrator comprises at least one system selected from an optical lens focusing system or a grating concentration system.

31. The equipment according to claim 18, wherein the optical monitor comprises CCD photodetector elements.

32. The equipment according to claim 21, comprising at least one optical fiber for conveying the optical radiation from the sensitive medium to the optical monitor.

33. The equipment according to claim 21, comprising a plurality of monitoring units, each having a respective sensitive medium for detecting a respective physico-chemical parameter of the medium.

34. The equipment according to claim 33, comprising a single optical photodetector connected to the plurality of monitoring units.

35. The equipment according to claim 33 or claim 34, comprising a plurality of light sources, each of which directs respective radiation at a respective one of the monitoring units of said plurality.

36. The equipment according to claim 33, comprising a plurality of optical detectors each associated with a respective one of the units of said plurality.

37. The equipment according to claim 33 or claim 36, comprising a single light source for directing optical radiation at the plurality of monitoring units.

38. The equipment according to claim 21, comprising an illuminating unit for illuminating the sensitive medium with optical radiation at least over the wavelength spectrum range.

39. The equipment according to claim 38, wherein the illuminating unit comprise solid-state photogenerator elements.

40. The equipment according to claim 39, wherein the illuminating unit comprises an array of solid-state photogenerator elements.

41. The equipment according to claim 40, wherein the array is a two-dimensional array.

42. The equipment according to claim 38, wherein the illuminating unit comprises a plurality of light-emitting diodes with respective emission characteristics distributed so as to be substantially without discontinuities over the wavelength spectrum.

43. The equipment according to claim 38, comprising a fiber optic for conveying the optical radiation generated by the illuminating unit to the sensitive medium.

44. The equipment according to claim 21, wherein the processor comprises:
(i) a memory unit for receiving a data base relating to the plurality of profiles of the spectrum of the at least one optical property over the wavelength spectrum range for different values of the at least one physico-chemical parameter;
(ii) an identifying unit for identifying, starting from the monitored signal and using a recognition procedure, a best-fit profile to the monitored profile from the plurality of profiles in the data base entered in the memory;
(iii) an indicator for indicating, as the detected value of the physico-chemical parameter, the value corresponding to the best-fit profile.

45. The equipment according to claim 44, wherein the recognition procedure determines the departures of the monitored profile from the optical property's spectra over the wavelength spectrum range.

46. The equipment according to claim 44, wherein the identifying unit determines the value of the respective physico-chemical parameter by interpolation as that corresponding to the minimum deviations of the profiles in the data base from the monitored profile.

47. The equipment according to claim 21, wherein the medium is blood.

48. The equipment according to claim 47, wherein the blood is in an extracorporeal circulatory system.

49. The equipment according to claim 21, wherein the medium is serum.

50. The equipment according to claim 21, wherein the equipment can monitor the value of the at least one physico-chemical parameter in real time.

51. A disposable unit for use in equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal and a plurality of predetermined profiles which correspond to a plurality of values of the at least one physico-chemical parameter a monitored datum indicative of the at least one respective physico-chemical parameter of the medium, wherein the monitored datum is derived from the monitored signal independent of any translational movement, amplification, attenuation, or displacement of the monitored profile of the spectrum of the at least one optical property of the sensitive medium, and wherein the disposable unit contains the sensitive medium.

52. The disposable unit according to claim 51, wherein the medium is blood.

53. The disposable unit according to claim 52, wherein the blood is in an extracorporeal circulatory system.

54. The disposable unit according to claim 51, wherein the medium is serum.

55. A method for determining the value of at least one physico-chemical parameter of a medium comprising:

(a) creating a data base containing a plurality of profiles of the spectrum of at least one optical property of a sensitive medium over a wavelength spectrum range for different values of the at least one physico-chemical parameter;

(b) entering the data base in a memory of a processing unit;

(c) providing a medium having at least one physico-chemical parameter;

(d) providing the sensitive medium having the at least one optical property in which a variation in at least one physico-chemical parameter of the medium produces a variation in a profile of a spectrum of the at least one optical property of the sensitive medium over at least one predetermined wavelength spectrum range of optical radiation;

(e) exposing the medium to the sensitive medium;

(f) monitoring the at least one optical property of the sensitive medium to obtain a monitored profile of the spectrum over the at least one predetermined wavelength spectrum range of optical radiation;

(g) identifying using a recognition procedure a best fit profile to the monitored profile from the plurality of profiles in the data base entered in the memory; and (h) indicating the value of the at least one physico-chemical parameter which corresponds to the best fit profile.

56. The method according to claim 55, wherein the medium is blood.

57. The method according to claim 56, wherein the blood is in an extracorporeal circulatory system.

58. The method according to claim 55, wherein the medium is serum.

59. The method according to claim 55, wherein the identifying step is carried out by determining the departures of the optical property's spectra over the wavelength spectrum range from the monitored profile.

60. The method according to claim 59, wherein the value of the at least one respective physico-chemical parameter is determined by interpolation as that corresponding to the minimum departures of the profiles of the plurality of profiles in the data base from the monitored profile.

61. A method for determining the value of at least one physico-chemical parameter of a medium comprising:

(a) providing a medium having at least one physico-chemical parameter;

(b) providing a sensitive medium having at least one optical property in which a variation in at least one physico-chemical parameter of the medium produces a variation in a profile of a spectrum of the at least one optical property of the sensitive medium over at least one predetermined wavelength spectrum range of optical radiation;

(c) exposing the medium to the sensitive medium;

(d) monitoring the at least one optical property of the sensitive medium to obtain a monitored profile of the spectrum over the at least one predetermined wavelength spectrum range of optical radiation;

(e) comparing the monitored profile of the spectrum of the at least one optical property with a plurality of predetermined profiles which correspond to a plurality of values of the at least one physico-chemical parameter of the medium; and (f) determining the value of the at least one physico-chemical parameter by comparing the monitored profile of the spectrum of the at least one optical property with the plurality of predetermined profiles, and wherein the physico-chemical parameter is selected from the group consisting of $pO_2$, $pCO_2$, pH, percent $O_2$ saturation, concentration of $K^+$, concentration of $Na^+$, and concentration of $Ca^{++}$.

62. The method according to claim 61, wherein the medium is blood.

63. The method according to claim 61, wherein the blood is in an extracorporeal circulatory system.

64. The method according to claim 61, wherein the medium is serum.

65. A method for determining the value of at least one physico-chemical parameter of a medium comprising:

(a) providing a medium having at least one physico-chemical parameter;

(b) providing a sensitive medium having at least one optical property in which a variation in at least one physico-chemical parameter of the medium produces a variation in a profile of a spectrum of the at least one optical property of the sensitive medium over at least one predetermined wavelength spectrum range of optical radiation;

(c) exposing the medium to the sensitive medium;

(d) monitoring the at least one optical property of the sensitive medium to obtain a monitored profile of the spectrum over the at least one predetermined wavelength spectrum range of optical radiation;

(e) comparing the monitored profile of the spectrum of the at least one optical property with a plurality of predetermined profiles which correspond to a plurality of values of the at least one physico-chemical parameter of the medium; and (f) determining the value of the at least one physico-chemical parameter by comparing the monitored profile of the spectrum of the at least one optical property with the plurality of predetermined profiles, and wherein the wavelength spectrum range is a wavelength spectrum range of polychromatic optical radiation substantially without discontinuities which extends over the wavelength range of between about 380 and about 1800 nanometers.

66. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal a monitored datum indicative of the at least one respective physico-chemical parameter of the medium, wherein the processor comprises:

(i) a memory unit for receiving a data base relating to a plurality of profiles of the spectrum of the at least one optical property over the wavelength spectrum range for different values of the at least one physico-chemical parameter;

(ii) an identifying unit for identifying, starting from the monitored signal and using a recognition procedure, a best-fit profile to the monitored profile from the plurality of profiles in the data base entered in the memory;

(iii) an indicator for indicating, as the detected value of the physico-chemical parameter, the value corresponding to the best-fit profile.

67. The equipment according to claim 66, wherein the medium is blood.

68. The equipment according to claim 67, wherein the blood is in an extracorporeal circulatory system.

69. The equipment according to claim 66, wherein the medium is serum.

70. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal and a plurality of predetermined profiles which correspond to a plurality of values of the at least one physico-chemical parameter a monitored datum indicative of the at least one respective physico-chemical parameter of the medium, wherein the monitored datum is derived from the monitored signal independent of any translational movement, amplification, attenuation, or displacement of the monitored profile of the spectrum of the at least one optical property of the sensitive medium, and wherein the equipment comprises a plurality of monitoring units, each having a respective sensitive medium for detecting a respective physico-chemical parameter of the medium.

71. The equipment according to claim 70, wherein the processor comprises:

(i) a memory unit for receiving a data base relating to the plurality of profiles of the spectrum of the at least one optical property over the wavelength spectrum range for different values of the at least one physico-chemical parameter;

(ii) an identifying unit for identifying, starting from the monitored signal and using a recognition procedure, a best-fit profile to the monitored profile from the plurality of profiles in the data base entered in the memory;

(iii) an indicator for indicating, as the detected value of the physico-chemical parameter, the value corresponding to the best-fit profile.

72. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal and a plurality of predetermined profiles which correspond to a plurality of values of the at least one physico-chemical parameter a monitored datum indicative of the at least one respective physico-chemical parameter of the medium, wherein the monitored datum is derived from the monitored signal independent of any translational movement, amplification, attenuation, or displacement of the monitored profile of the spectrum of the at least one optical property of the sensitive medium, and wherein the equipment comprises a plurality of monitoring units, each having a respective sensitive medium for detecting a respective physico-chemical parameter of the medium, and wherein the equipment comprises a single optical photodetector connected to the plurality of monitoring units.

73. The equipment according to claim 72, wherein the processor comprises:

(i) a memory unit for receiving a data base relating to the plurality of profiles of the spectrum of the at least one optical property over the wavelength spectrum range for different values of the at least one physico-chemical parameter;

(ii) an identifying unit for identifying, starting from the monitored signal and using a recognition procedure, a best-fit profile to the monitored profile from the plurality of profiles in the data base entered in the memory;

(iii) an indicator for indicating, as the detected value of the physico-chemical parameter, the value corresponding to the best-fit profile.

74. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal and a plurality of predetermined profiles which correspond to a plurality of values of the at least one physico-chemical parameter a monitored datum indicative of the at least one respective physico-chemical parameter of the medium, wherein the monitored datum is derived from the monitored signal independent of any translational movement, amplification, attenuation, or displacement of the monitored profile of the spectrum of the at least one optical property of the sensitive medium, and wherein the equipment comprises a plurality of monitoring units, each having a respective sensitive medium for detecting a respective physico-chemical parameter of the medium, and wherein the equipment comprises a plurality of optical photodetectors, each associated with a respective one of the units of the plurality of monitoring units.

75. The equipment according to claim 74, wherein the processor comprises:

(i) a memory unit for receiving a data base relating to the plurality of profiles of the spectrum of the at least one optical property over the wavelength spectrum range for different values of the at least one physico-chemical parameter;

(ii) an identifying unit for identifying, starting from the monitored signal and using a recognition procedure, a best-fit profile to the monitored profile from the plurality of profiles in the data base entered in the memory;

(iii) an indicator for indicating, as the detected value of the physico-chemical parameter, the value corresponding to the best-fit profile.

76. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal and a plurality of predetermined profiles which correspond to a plurality of values of the at least one physico-chemical parameter a monitored datum indicative of the at least one respective physico-chemical parameter of the medium, wherein the monitored datum is derived from the monitored signal independent of any translational movement, amplification, attenuation, or displacement of the monitored profile of the spectrum of the at least one optical property of the sensitive medium, and wherein the equipment comprises a plurality of monitoring units, each having a respective sensitive medium for detecting a respective physico-chemical parameter of the medium, and wherein the equipment comprises a single light source for directing optical radiation at the plurality of monitoring units.

77. The equipment according to claim 76, wherein the processor comprises:

(i) a memory unit for receiving a data base relating to the plurality of profiles of the spectrum of the at least one optical property over the wavelength spectrum range for different values of the at least one physico-chemical parameter;

(ii) an identifying unit for identifying, starting from the monitored signal and using a recognition procedure, a best-fit profile to the monitored profile from the plurality of profiles in the data base entered in the memory;

(iii) an indicator for indicating, as the detected value of the physico-chemical parameter, the value corresponding to the best-fit profile.

78. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal and a plurality of predetermined profiles which correspond to a plurality of values of the at least one physico-chemical parameter a monitored datum indicative of the at least one respective physico-chemical parameter of the medium, wherein the monitored datum is derived from the monitored signal independent of any translational movement, amplification, attenuation, or displacement of the monitored profile of the spectrum of the at least one optical property of the sensitive medium, and wherein the equipment comprises a plurality of monitoring units, each having a respective sensitive medium for detecting a respective physico-chemical parameter of the medium, and wherein the equipment comprises a plurality of light sources, each of which directs respective optical radiation at a respective one of the monitoring units of said plurality.

79. The equipment according to claim 78, wherein the equipment comprises a single optical photodetector connected to the plurality of monitoring units.

80. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal a monitored datum indicative of the at least one respective physico-chemical parameter of the medium, wherein the processor comprises:

(i) a memory unit for receiving a data base relating to a plurality of profiles of the spectrum of the at least one optical property over the wavelength spectrum range for different values of the at least one physico-chemical parameter;

(ii) an identifying unit for identifying, starting from the monitored signal and using a recognition procedure, a best-fit profile to the monitored profile from the plurality of profiles in the data base entered in the memory;

(iii) an indicator for indicating, as the detected value of the physico-chemical parameter, the value corresponding to the best-fit profile, wherein the recognition procedure determines the departures of the monitored profile from the optical property's spectra over the wavelength spectrum range.

81. Equipment for monitoring the value of at least one physico-chemical parameter of a medium using a sensitive medium having at least one optical property that varies in dependence on the at least one physico-chemical parameter of the medium, the equipment comprising:

(a) at least one monitoring unit with a part containing the sensitive medium in which a variation in the at least one physico-chemical parameter of the medium produces a variation in a profile of a spectrum of the at least one optical property of the sensitive medium over at least one predetermined wavelength spectrum range of optical radiation;

(b) an optical monitor which produces a monitored signal and is sensitive to optical radiation over the at least one predetermined wavelength spectrum range, whereby the monitored signal is indicative of a monitored profile of the at least one optical property of the sensitive medium over the at least one predetermined wavelength spectrum range; and (c) a processor for deriving from the monitored signal a monitored datum indicative of the at least one respective physico-chemical parameter of the medium, wherein the processor comprises:

(i) a memory unit for receiving a data base relating to a plurality of profiles of the spectrum of the at least one optical property over the wavelength spectrum range for different values of the at least one physico-chemical parameter;

(ii) an identifying unit for identifying, starting from the monitored signal and using a recognition procedure, a best-fit profile to the monitored profile from the plurality of profiles in the data base entered in the memory;

(iii) an indicator for indicating, as the detected value of the physico-chemical parameter, the value corresponding to the best-fit profile, wherein the identification unit determines the value of the respective physico-chemical parameter by interpolation as that corresponding to the minimum deviations of the profiles in the data base from the monitored profile.

* * * * *